United States Patent [19]

Johnson et al.

[11] 3,932,392
[45] Jan. 13, 1976

[54] PROCESS FOR THE PREPARATION OF 7-AMINOCEPHALOSPORANIC ACIDS

[75] Inventors: David A. Johnson, Fayetteville;
Steven P. Brundidge, Wolcott;
Albert L. Vulcano, Liverpool;
Chester Sapino, Jr., East Syracuse;
James Mahan; Joseph H. Grossman,
both of Syracuse, all of N.Y.

[73] Assignee: Bristol-Myers Company, New York, N.Y.

[22] Filed: Jan. 14, 1974

[21] Appl. No.: 433,336

[52] U.S. Cl............ 260/243 C; 424/246; 260/239.1
[51] Int. Cl.².............. C07D 279/08; C07D 501/18
[58] Field of Search................................ 260/243 C

[56] References Cited
UNITED STATES PATENTS

| | | | |
|---|---|---|---|
| 3,725,397 | 4/1973 | Graham et al. | 260/243 C |
| 3,725,399 | 4/1973 | Ellerton et al. | 260/243 C |

*Primary Examiner*—Nicholas S. Rizzo
*Assistant Examiner*—Mark L. Berch
*Attorney, Agent, or Firm*—Robert E. Havranek

[57] ABSTRACT

7-Aminocephalosporanic acid (7-ACA) and 7-amino-3-methyl-3-cephem-4-carboxylic acid (7-ADCA) are valuable intermediates in the preparation of semi-synthetic cephalosporins. These compounds are commonly prepared by cleaving the amide bond of compounds having the formula

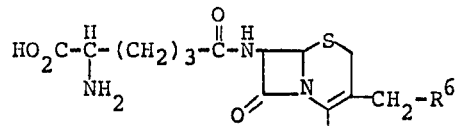

Ia or

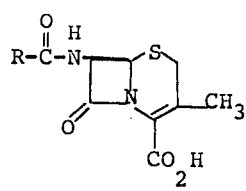

IIa in which $R^6$ is H or

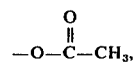

R is the side chain of a known penicillin, especially phenoxymethyl or benzyl, and the amino and carboxyl functions are blocked; by A. halogenating the blocked compounds Ia or IIa to produce an imino-halide;

B. forming an imino-ether from the imino-halide by treatment with an alcohol; and C. mixing said imino-ether with water or an alcohol to produce 7-aminocephalosporanic acid or 7-amino-3-methyl-3-cephem-4-carboxylic acid.

The invention claimed is the use of dicyclohexylamine or diisopropylamine instead of a tertiary amine acid scavenger in step A.

11 Claims, No Drawings

PROCESS FOR THE PREPARATION OF 7-AMINOCEPHALOSPORANIC ACIDS

BACKGROUND OF THE INVENTION

1. Field of the Invention:

This invention relates to a more ecologically desirable and safe procedure for cleaving cephalosporins and then recovering the acid scavenger required in the cleavage process.

2. Description of the Prior Art:

Several processes for the chemical cleavage of cephalosporin C or certain of its derivatives are described in the patent literature (U.S. Pat. Nos. 3,188,311, 3,234,223, 3,124,576, 3,573,296, 3,573,295 and 3,697,515 and British Pat. No. 1,041,985. None of these processes employ or teach acid scavengers other than tertiary amines.

SUMMARY OF THE INVENTION

This invention relates to the use of two secondary amine acid scavengers in the cleavage of compounds Ia and IIa to produce 7-ACA or 7-ADCA.

7-aminocephalosporanic acid (7-ACA) and 7-amino-3-methyl-3-cephem-4-carboxylic acid (7-ADCA) are available intermediates in the preparation of a multitude of semisynthetic cephalosporanic acid antibacterial agents. Commercial supplies of 7-ACA and 7-ADCA are prepared by the chemical degradation of either naturally occurring cephalosporanic acids, i.e., cephelosporin C or penicillins rearranged by the sulfoxide process (thermal rearrangement) to produce compounds such as 7-phenoxyacetamido-3-methyl-3-cephem-4-carboxylic acid.

Most 7-ACA is derived from cephalosporin C (U.S. Pat. No. 3,093,638) which has the structure The production of 7-ACA by currently available methods is fraught with difficulties from the fermentation step to the chemical cleavage of cephalosporin C.

Because of its highly ionic nature, cephalosporin C is extremely difficult to harvest by solvent extraction of the fermentation broth. Methods have been devised to improve recovery by the in situ formation of N-acylated cephalosporin C derivatives (see U.S. Pat. No. 3,573,296 and 3,573,295), which are then solvent extractable and usable as such or after purification in the subsequent preparation of 7-ACA.

It was found in U.S. Pat. Nos. 3,473,295 and 3,573,296 that haloformate derivatives and isocyanate derivatives having the formula

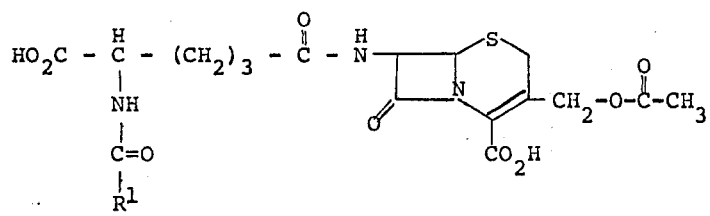

III wherein $R^1$ is —O—$R^2$ or —NH—$R^2$ in which $R^2$ is (lower)alkyl or aryl having the formula

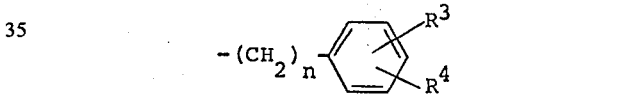

in which n is an integer of 1 to 6 and $R^3$ and $R^4$ are alike or different and each is H, Cl, Br, F, $NO_2$, (lower)alkyl or (lower)alkoxy can be prepared in situ in whole fermentation broth and then be extracted from the aqueous phase by organic solvent extraction. The N-blocked cephalosporin C was then isolated as the sodium salt but the purity was often less than desirable. It was subsequently found (as disclosed by our colleague Thomas J. Brooks, Jr. in U.S. application Ser. No. 283,887) that N-Carbisobutoxycephalosporin C could be conveniently purified by recrystallization as the di(dicyclohexylamine) salt in 97% purity.

Subsequent studies showed the di(dicyclohexylamine) salt of N-carbisobutoxycephalosporin C could be used directly in the silylation step of the cleavage reaction to block two carboxyl groups, e.g.

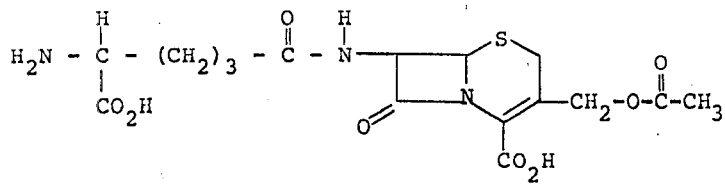

I.

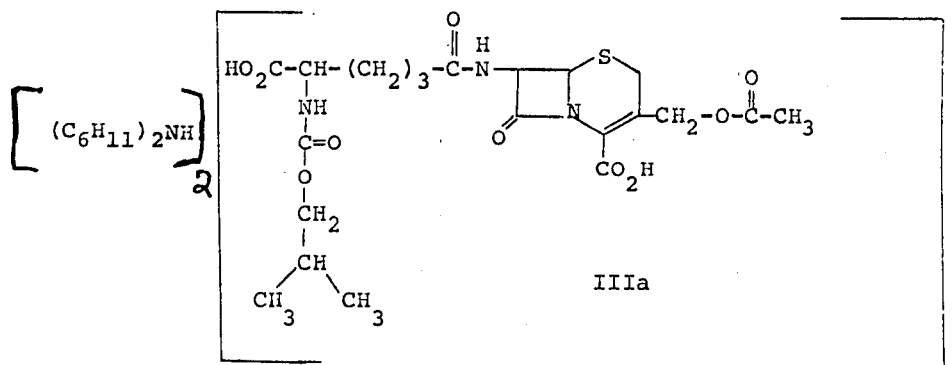

IIIa

Excess $(CH_3)_2SiCl_2$

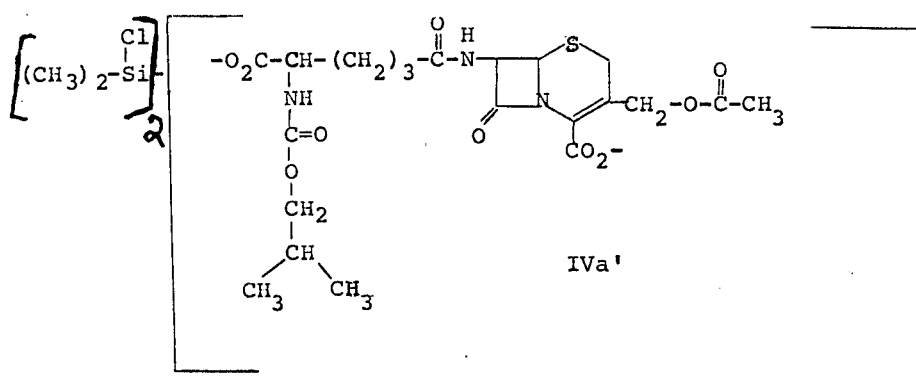

IVa' and/or

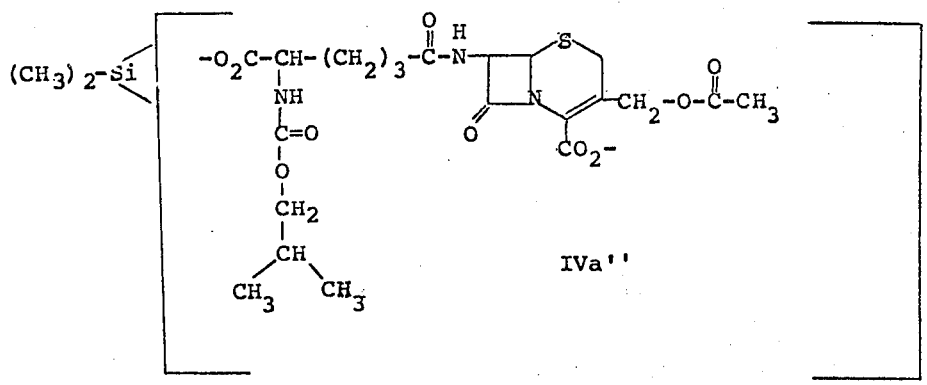

IVa'' and/or possibly some IVa''' consisting of

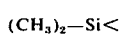

linked by ester formation to 2 carboxyl groups of 2 molecules of IIIa. For simplicity, formula IVa' is representative of all the possible silyl esters so produced by the reaction.

The yields of compound IVa using the di (dicyclohexylamine) salt of compound IIIa were found to be approximately as good as those obtained using a tertiary amine, e.g., triethylamine or dimethylaniline. That is to say, the secondary amine, dicyclohexylamine, did not prevent formation of the silyl esters of compound IIIa.

The discovery of this unexpected result stimulated the investigation of the possibility of using dicyclohexylamine as the acid scavenger in the formation of the iminohalide derivative of compound Va formed by the interaction of compound IVa with phosphorous petachloride.

Accordingly, compound IVa was treated with phosphorous pentachloride in the presence of dicyclohexylamine in a molar ratio of 1:1.25:2.44 (compound IVa: $PCl_5$: dicyclohexylamine) at about $-45°C$. Analytical studies indicated the formation of compound Va having the structure

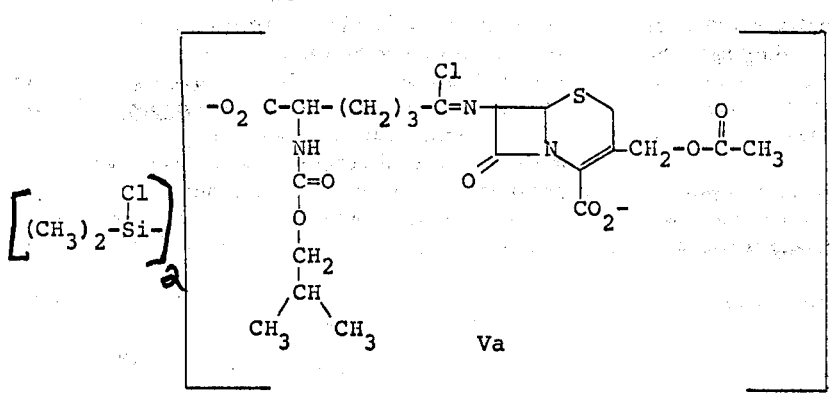

Va

Compound Va, in situ was cooled to −60°C and chilled methanol was added with stirring to produce the compound VIa, which was identified by analytical studies, i.e.,

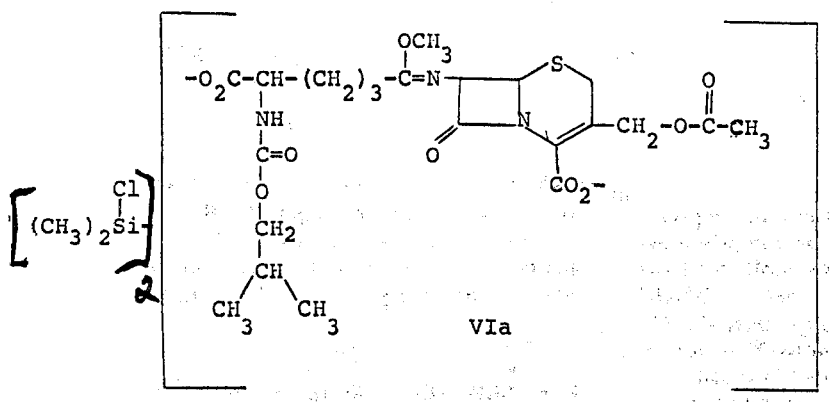

VIa

Treatment of VIa with 50% aqueous methanol at −40°C produced 7-ACA in 76% yield.

The discovery that it is possible to use a secondary amine as the acid scavenger in this cleavage reaction was a pleasant and unexpected surprise.

Chemically, one would expect dicyclohexylamine to react competitively with the PCl$_5$ used therein to produce phosphorous compounds of the formulas, for example,

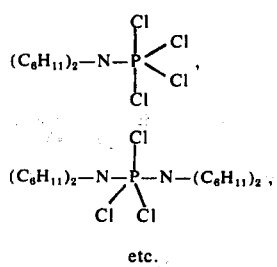

etc.

If the dicyclohexylamine so reacted with the PCl$_5$, the PCl$_5$ would be available to form the imino-halide compound Va and the dicyclohexylamine would be unavailable as an acid scavenger for that HCl generated by the PCl$_5$ that did react with compound IVa to form compound Va.

It is probable that there is some interaction of the PCl$_5$ and dicyclohexylamine taking place, but it is either insignificant or reversible and as such has no effect on the main reaction between compound IVa and the PCl$_5$.

A second chemical reaction can occur between secondary amines and imino-halides. The secondary amine is normally expected to react with imino-halides to produce an amidine, e.g.,

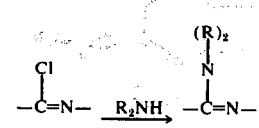

The amidines so produced would be stable to hydrolysis and would not produce 7-ACA under the conditions employed.

Thus the failure of dicyclohexylamine to so react with the imino-halide Va was also an unexpected result.

Subsidiary benefits of this discovery are the commercially desirable ones which include:

1. the excellent recovery of dicyclohexylamine from the reaction process, thereby resulting in decreased costs and a lesser pollution of the environment. 2. a safer process because it means the use of less volatile dicyclohexylamine instead of dimethylaniline, a notoriously toxic chemical.

Subsequent experiments, as illustrated in the examples, indicate the cleavage reaction works substantially as well using dicyclohexylamine as the acid scavenger as does the use of a tertiary amine such as pyridine, triethylamine or dimethylaniline. Furthermore, it was subsequently found that diisopropylamine can also be used as the acid scavenger. The yields with either amine is in the range of 55 to 89% depending upon the molar ratios of the reactants so used. The use of dicyclohexylamine appears to have the advantage over diisopropylamine in that it is more easily recovered and purified for recycling in the process.

The process using dicyclohexylamine or diisopropylamine is completely adaptable to the cleavage of compound having the formula IIa, especially when R is phenoxymethyl or benzyl.

7-aminocephalosporanic acid has the structure

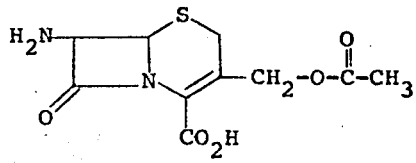

7-amino-3-methyl-3-cephem-4-carboxylic acid has the structure

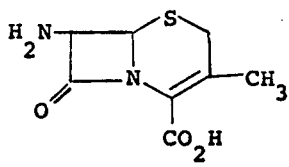

The term "(lower)alkyl" for the purpose of the present invention is defined as an alkyl group comprised of 1 to 10 carbon atoms, including for example, methyl, ethyl n-propyl, isopropyl, n-butyl, isobutyl, t-butyl, n-pentyl, etc., and the like, but especially methyl, ethyl, n-propyl, isopropyl, n-butyl and isobutyl. The terms "(lower)alkoxy" and "halo(lower)alkyl" are also defined as moieties containing 1 to 10 carbon atoms.

A preferred embodiment of the instant invention is the process for the preparation of a compound having the formula

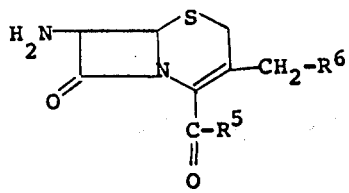

in which $R^6$ is H or acetoxy and $R^5$ is OH or the residue of an acid blocking group, which process comprises treating a compound having the formula

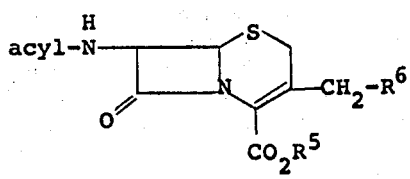

XX in which $R^6$ is H or acetoxy, $CO_2R^5$ is a carboxyl group blocked to convert it into a group not reacting with the acid halide used for forming the imino-halide, and acyl is the residue of a carboxylic acid; with an acid halide to form an imino-halide, converting the imino-halide into an imino-ether by means of treating the imino-halide with an alcohol and splitting the imino-ether double bond with a compound containing a hydroxy group; the improvement of which comprises using diisopropylamine or dicyclohexylamine as the acid scavenger in the imino-halide forming step.

A more preferred embodiment is the process for the preparation of a compound having the formula

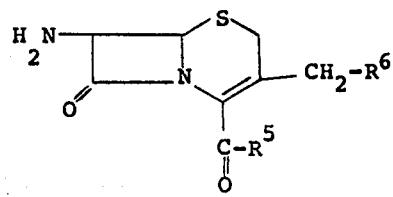

in which $R^6$ is H or acetoxy and $R^5$ is OH or OY in which Y is alkyl of 1 to 10 carbon atoms, a radical of the formula

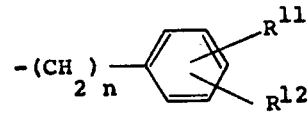

in which n is an integer of 0 to 6 and $R^{11}$ and $R^{12}$ are alike or different and each is H, Cl, Br, F, $NO_2$, (lower)alkyl or (lower)alkoxy, or Y is 2,2,2-trichloroethyl, methoxymethyl and pivaloyloxymethyl; which process comprises treating a compound having the formula

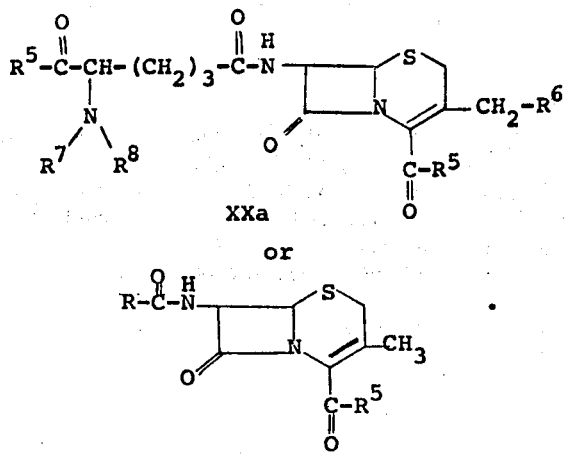

wherein $R^6$ is H or acetoxy, R is the side chain of a known fermentable penicillin, $R^7$ is H, $R^8$ is alkanoyl of 2 to 20 carbons, but preferably 2 to 6 carbons, or $R^8$ is a radical of the formula

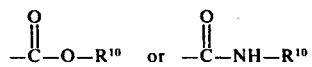

in which $R^{10}$ is alkyl of 1 to 6 carbons or a group of the formula

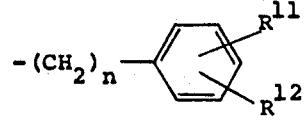

wherein n is an integer of 0 to 6 and $R^{11}$ and $R^{12}$ are alike or different and each is H, Cl, Br, F, $NO_2$, (lower)alkyl or (lower) alkoxy, or $R^8$ is trichloroacetyl, chloroacetyl, phenylacetyl or benzoyl, or when $R^7$ and $R^8$ are taken together an o-phthaloyl group; $R^5$ is —OY in which Y is alkyl of 1 to 10 carbon atoms, a radical of the formula

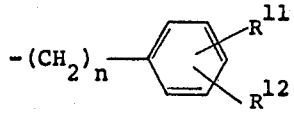

is which n is an integer of 0 to 6 and $R^{11}$ and $R^{12}$ are alike or different and each is H, CL, Br, F, $NO_2$, (lower)alkyl or (lower)alkoxy; or Y is —$CH_2$—$CCl_3$, —Si$(CH_3)_2$Cl, —Si$(CH_3)_3$ or

with an acid halide to form an imino-halide, converting the imino-halide into an imino-ether by means of treating the imino-halide with an alcohol, and splitting the imino-ether double bond by the addition of water; the improvement which comprises using diisopropylamine or dicyclohexylamine as the acid scavenger in the imino-halide forming steps.

A preferred embodiment of the instant invention is the process for the preparation a compound having the formula

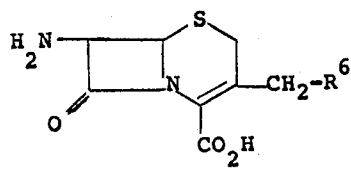

in which $R^6$ is H or acetoxy; which process comprises treating a compound having the formula

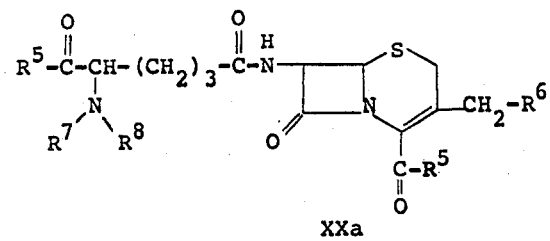

XXa or

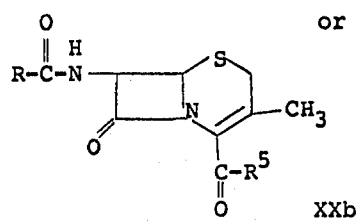

XXb wherein $R^6$ is H or acetoxy, R is phenoxymethyl or benzyl, $R^7$ is H, $R^8$ is alkanoyl of 2 to 6 carbons, a radical of the formula

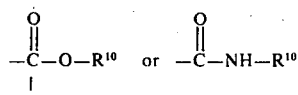

in which $R^{10}$ is alkyl of 1 to 6 carbons or a group of the formula

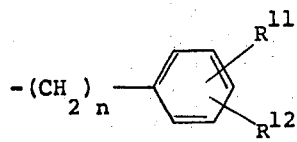

wherein n is an integer of 0 to 6 and $R^{11}$ and $R^{12}$ are alike or different and each is H, Cl, Br, F, $NO_2$, (lower)alkyl or (lower)alkoxy, or $R^8$ is trichloroacetyl, chloroacetyl, phenylacetyl or benzoyl, or when $R^7$ and $R^8$ are taken together an o-phthaloyl group and $R^5$ is

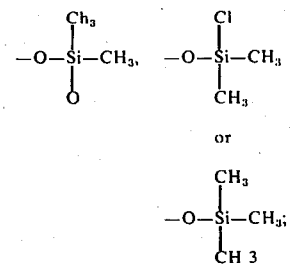

with an acid halide to form an iminohalide, converting the imino-halide into an imino-ether by means of treating the imino-ether with a (lower)alkanol, and splitting the imino-halide double bond by treatment with water; the improvement of which comprises using diisopropylamine or dicyclohexylamine as the acid scavenger in the imino-halide forming step.

The most preferred embodiment is the process for the preparation of 7-aminocephalosporanic acid from compound XXa in which $R^6$ is acetoxy, $R^7$ is H, $R^8$ is carbisobutoxy,

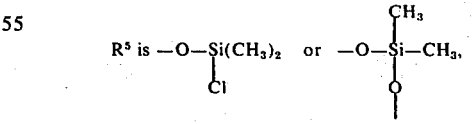

the reaction solvent is methylene chloride, the acid halide is phosphorous pentachloride, the (lower)alkanol is methanol and the acid scavenger is dicyclohexylamine.

Another most preferred embodiment is the process for the preparation of 7-amino-3-methyl-3-cephem-4- carboxylic acid from compound XXb in which R is phenoxymethyl, R⁵ is

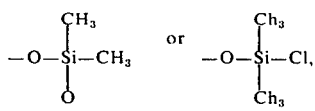

the solvent of reaction is methylene chloride, the acid halide is phosphorous pentachloride, the (lower)alkanol is methanol and the acid scavenger is dicyclohexylamine.

In the starting materials XX, 7-N-acyl group is the acyl group of any mono- or dicarboxylic acid, especially the δ-aminoadipoyl group of which the free amino and carboxyl groups are blocked.

Groups useful for the blocking of the free amino and carboxyl groups occurring in 7-acyl radicals are known in the art, especially from the field of aminoacids and peptides. It should, however, be noted, that in the present reaction the whole acyl residue is split off and rejected and that, therefore, there is no need to use blocking groups which can be split off after the reaction has been carried out. Useful for blocking the amino group is, for example, a lower alkyl, aryl or acyl radical, advantageously a radical which reduces the basicity of the amino group. The aryl radicals may be substituted. Especially suitable are the 2:4-dinitrophenyl, the 2:4:6-trinitrophenyl, the 2:4-dinitro-6-methoxy-phenyl, the 4-cyanophenyl and the 4-carbomethoxyphenyl radical. Acyl are more especially lower alkanoyl radical with one to six carbon atoms, for example acetyl, propionyl, butyryl, also aroyl radicals, such as benzoyl, as well as benzoyl substituted by nitro, cyano, sulfo groups, halogen atoms, lower alkyl or lower alkoxy groups, and preferably N:N-phthaloyl; further, arylower alkanoyl radicals, such as phenylacetyl, or the benzenesulfonyl or toluenesulfonyl radical may be used for blocking the amino group. The amino groups can also be blocked by protonation.

The free carboxyl group is, for instance, blocked by esterification. As in the case of amino groups occurring in the acyl radical, also a carboxyl group occurring in the acyl radical can be blocked in suitable way and there is no critical point in this regard as the whole acyl residue is split off in the reaction. Thus, esters with hydroxy compounds can be used, for example, with alcohols such as unsubstituted or substituted alcohols or phenols. In most cases, it will be preferred to start with compounds in which a carboxyl group occurring in the 7-acyl residue is blocked in the same way as the carboxyl group in 4-position of the dihydrothiazine ring. Hydroxy compounds suitable for that purpose are indicated for illustration below. It is, however, also possible, especially in the case of the δ-aminoadipolyl residue, to block the amino and carboxyl group together, for example by reaction with isocyanates or isothiocyanates with formation of a hydantoin or thiohydantoin ring.

If, in the starting material of formula XX, the 7-acyl group is the blocked δ-aminoadipoyl group, the compound is derived from Cephalosporin C. Other 7-acylaminocephalosporanic acids or derivatives thereof, respectively, can also be used as starting materials for the new process. Thus, the acyl group can be an aliphatic, aromatic heterocyclic, araliphatic or heterocyclicaliphatic carboxylic acid radical, especially the acyl radical of naturally occurring 7-acylaminocephalosporanic acids and 6-acylaminopenicillanic acids [that can be prepared starting from naturally occurring cephalosporins or penicillins], for example cephalosporin C or 6-(δ-amino-adipoyl)amino penicillanic acid, penicillin G, V, F, dihydro-F, K, X or O. In the starting compounds of formula XX, the carboxyl group occurring in 4-position is blocked during the reaction with the imino-halide forming agent. The purpose of the blocking is to avoid the carboxyl group being halogenated by that agent, for instance phosphorous pentachloride. As blocking groups, therefore, any compound may be used, which converts the carboxyl group into a group not reacting with that agent. If the 7-desacylated compound is to be isolated in the form of the free carboxylic acid, a blocking group should be used which can be split off without destruction of the cephalosporin nucleus. Such blocking groups are, for instance, ester groups that can be split in an acidic or neutral or weakly basic (up to pH9) reaction medium, for instance, by reduction, solvolysis, for instance acid hydrolysis or photolysis. Advantageously, the carboxyl group is esterified with hydroxy compounds known in the field of aminoacids and peptides to be readily eliminable from the ester especially in a non-alkaline medium. Such hydroxy compounds derive from elements of the fourth group (IV A) of the periodic system having an atom weight of at most 120, for instance from carbon, silicon, germanium or tin. For illustration, methanol substituted by at least one phenyl group which phenyl may be substituted by one or more substituents selected from the group consisting of halogen atoms such as chlorine, bromine, fluorine, iodine, lower alkyl, lower alkoxy, especially methoxy, or the nitro group, for instance, benzylalcohol, diphenylmethanol, triphenylmethanol, para-methoxyphenylmethanol 3,5-dimethoxy-benzylalcohol, di-paramethoxyphenyl-methanol, para-nitrobenzylalcohol, 2,4,6-trimethylbenzylalcohol, 3,4-dimethoxy-6-nitro-benzylalcohol, α-phenyl-α-(3,4-dimethoxy-6-nitrophenyl)-methanol, α-methyl-α-(3,4 -dimethoxy-6-nitrophenyl)-methanol, further methanol substituted by three lower alkyl groups such as tertiary butanol, tertiary amylalcohol or ethanol, substituted by 3 halogen atoms in 2-position, e.g. trichloroethanol, tribromethanol; further 2-iodoethanol, tetrahydropyranol, stannylalcohol.

As mentioned above, the blocking group has to be present only during the step of formation of the imide halide. After that step it can be split off, if desired. This splitting can be effected by solvolysis, for instance with water or alcohols, if desired in an acidic or weakly alkaline medium, or by reduction, for instance with hydrogen in the presence of a catalyst or with metals such as zinc, or finally, by photolysis, preferably in a polar medium.

A blocking ester group can also be retained if it is split enzymatically in the tissue on administration of the compound.

Agents forming imido-halides are, more especially acid halides, particularly chlorides, which are derived from phosphorus, sulfur, carbon or their oxygen acids, for example phosphorus oxychloride, phosphorus pentachloride, phosphorus trichloride, thionyl chloride, phosgene and oxalyl chloride The imino-halide is reacted with an alcohol to form an imino-ether. Alcohols are, for example, lower alkanols such as ethanol, n-propanol, isopropanol n-butanol, especially methanol, phenyl lower alkanols, for instance, benzyl alcohol, or (lower)alkyldiols, such as propylene or ethylene glycol. The iminoether is an intermediate which need not be isolated but can be split in the same reaction medium.

The splitting of the C=N double bond of the iminoether to form the compound XXX is carried out with a compound containing a hydroxyl group such as water or an alcohol, for instance, that alcohol used for forming the iminoether, or with a mixture of alcohol with water, preferably at a pH from 0 to 4.

Other examples of what acyl can represent in compounds XX are the radical having the formula

in which $n$ represents an integer of 0 to 4, preferably 1, and in which a $CH_2$-group, especially in $\alpha$-position may be substituted, for instance by amino, halogen, lower alkoxy, cyan, nitro or carboxyl, and $R_2$ represents an unsubstituted or substituted aryl, cycloalkyl, or heterocyclyl radical or an aryloxy, arylthio, cycloalkoxy, heterocyclyloxy or heterocyclylthio radical, the aryl or heterocyclyl radicals being monocyclic or dicyclic, for example 2:6-dimethoxy-benzoyl, tetrahydronaphthoxyl, 2-methoxynaphthoyl, 2-ethoxy-naphthoxyl, 3-pyridyl-benzoyl, phenylacetyl, phenylglycyl, phenylalanyl, phenylcyanacetyl, p-chlorophenyl-cyanacetyl, phenoxyacetyl, S-phenyl-thioacetyl, S-bromophenyl-thioacetyl, $\alpha$-phenoxypropionyl, $\beta$-phenoxypropionyl, $\alpha$-phenoxy-phenylacetyl, $\alpha$-methoxyphenylacetyl, $\alpha$-methoxy-3:4-dichlorophenyl-acetyl, pyridyl(3)-acetyl, pyridyl(20)-acetyl, 1-methyl-imidazolyl(2)-thioacetyl, 1,2,4-triazolyl(3)-thioacetyl, thiolinyl(2)-thioacetyl, imidazolinyl(2)-thioacetyl, 1-methylimidazoly(1)-acetyl, benzyloxy-carbonyl, S-benzylthioacetyl, S-benzylthiopropionyl, hexahydrobenzyloxycarbonyl, cyclopentanoyl, cyclohexanoyl, 2-thienylacetyl, 2-thienyl-cyanacetyl, 3-thienylacetyl, 2-furylacetyl, 2-indoylacetyl, 2-phenyl-5-methyl-isoxazoly-carbonyl, 2-(2'-chlorophenyl)-5-methyl-isoxazolyl carbonyl, indenyl-carbonyl, or a radical of the formula

in which $n$ represents an integer of 1 to 7, and the chain is straight or branched and, if desired, is interrupted by an oxygen atom or a sulfur atom or is substituted, for instance, by halogen, cyan, carboxy, carbalkoxy, lower alkoxy, nitro or amino, for example, a propionyl, butyryl, hexanoyl, oxtanoyl, butylthioacetyl, acrylyl, $\alpha$-cyano-$\beta$-dimethyl-acroyl, crotonyl, 2-pentenoyl, allylthioacetyl, chloroacetyl, $\beta$-bromopropionyl, dichloroacetyl, dibromacetyl, difluoroactyl, ethoxycarbonylacetyl, dimethoxycarbonylacetyl, cyanacetyl, $\alpha$-cyanopropionyl, nitroacetyl, aminoacetyl, or $\alpha$-carboxylpropionyl radical.

EXAMPLES

EXAMPLE 1

Preparation of 7-aminocephalosporanic acid via dicyclohexylamine

N-Carbisobutoxycephalosporin C di(dicyclohexylamine) salt (IIIa, 10 g.) was added to 150 ml of dry methylene chloride, followed by 3.5 ml. of dichlorodimethylsilane over a 10 minute period with stirring. Two additional 10 gram portions of IIIa were added to the resultant slurry, followed each time by 3.5 ml of dichlorodimethylsilane. The final slurry was aged for 30 minutes with vigorous stirring and then brought to 240 ml volume with additional methylene chloride. A sample of the slurry was determined to be the desired disilyl ester of N-carbisobutoxycephalosporin C (IVa).

A one-third portion of the slurry (11.38 mmoles of the IVa ester) was treated with 5.73 ml (27.77 mmoles) of dicyclohexylamine. The resultant slurry was cooled to −45° C and 3 g. (14.23 mmoles) of finely ground $PCl_5$ was added with stirring and continued cooling. The temperature surged to −35° C and the chlorination slurry was cooled back to −40° C and held there for 15 minutes. The chlorination mix was cooled to −60° C and 40 mls of precooled methanol (−70° C) was added all at once. The mixture was aged with stirring for 120 minutes at −40° C.

Ice cold 50% aqueous methanol (16.8 ml) was added to the −40°C mixture. The temperature rose to −10° C and was held in the range of −10 to −40° C for 25 minutes. The mixture was warmed to 0° C and dripped into 140 ml of methanol and 28 ml of water keeping the mixture at constant pH 3.6 with $NH_4OH$.

The 7-ACA slurry so produced was stirred for 60 minutes at 5 to 10° C, then filtered and washed with ice cold water and methanol. The yield was 2.37 g. of 97% pure 7-ACA (76.7%).

Concentration in vacuo or at atmospheric pressure of the mother liquors leaves a post residue consisting of essentially dicyclohexylamine hydrochloride, water and unreacted or decomposed cephalosporin C by-products. Basification of the pH to about 9 with sodium hydroxide, followed by physical separation of the two layers produces essentially pure dicyclohexylamine in about 85–95% recofery of theory.

EXAMPLE 2

Preparation of 7-ACA via dicyclohexylamine

Compound IIIa (40 g, 45.55 mmoles) was suspended in dry methylene chloride (400 ml) followed by the addition of dichlorodimethylsilane (14.0 ml, 14.89 g, 116.03 mmoles) at 25° under a nitrogen atmosphere. The slurry was stirred at 25° for 1 hour and cooled to −40°. Dicyclohexylamine (45.36 ml, 41.28 g. 227.66 mmoles) dissolved in methylene chloride to a total volume of 120 mls was added slowly to the ester slurry at −40°. After 20 ml of the amine was added, finely ground phosphorous pentachloride (20.86 g, 100.16 mmoles) was added in one portion to the slurry. The temperature rose 5°–8° during the addition of the phosphorous pentachloride. The remainder of the amine solution was added slowly over a 30–40 minute period and chlorination was allowed to proceed for 2 hours at −30 to −40°. The slurry was cooled to −50° and precooled (−60°) methanol (46.2 ml., 36.5 g, 1.138 moles) was added over 15–20 minutes maintaining the temperature below −40°. Methylation was allowed to proceed for 1 ½ hours at −40°. Methanol (150 ml) was rapidly added and the mixture stirred at −35 to −40° for 0.5 hours. Water (25.0 ml) was added at −35° and the mixture stirred at this temperature at −35° for 1 hour. The slurry was warmed to 0°–5°. Water (30.0 ml) and methanol (200 ml) were added until all of the dicyclohexylamine hydrochloride dissolved. A portion of the batch (0.33 volume) was cyrstallized by pH adjustment with 6N ammonium hydroxide at 0°–5°. The remainder of the solution was added to the 7-ACA slurry over a 30–40 minute period maintaining the pH at 3.4–3.6. After the addition, the slurry was stirred for 1 hour at 0°–5° holding the pH at 3.6. The slurry was filtered, washed with methanol and dried at 40°–50°: 9.43 g (76%). Infrared and NMR spectra were consistent for structure. The yield corrected for input cephalosporin potency and output 7-ACA potency is 10.28 g., 83%. The material assayed at 966 mcg/mg by chemical assay.

EXAMPLE 3

Preparation of 7-ACA via diisopropylamine

Compound IIIa (20.0g, 22.77 mmoles) was suspended in dry methylene chloride (200 ml) followed by the addition of dichlorodimethylsilane (7.0 ml, 7.49 g, 58.02 mmoles) at 25° C under a nitrogen atmosphere. The slurry was stirred at 25° C for 1 hour and cooled to −40° C. Diisopropylamine (15.96 ml, 11.52 g, 113.86 mmoles) dissolved in methylene chloride to a total volume of 60 ml was added slowly to the ester slurry at −40° C. After 10 ml of the amine was added, finely ground phosphorus pentachloride (10.43 g, 40.98 mmoles) was added in one portion to the slurry. The temperature rose 5°–8° during the addition of the phosphorus pentachloride. The remainder of the amine solution was added slowly over a 30–40 minute period and chlorination was allowed to proceed for 2 hours at −30° to −40° C. The slurry was cooled to −50° C and precooled (−60°)methanol (23.1 ml, 18.3 g, 569.3 mmoles) was added over a 15–20 minute period maintaining the temperature below −40° C. Methylation was allowed to proceed for 1 ½ hours at −40° C. Methanol (50 ml) was rapidly added and the mixture stirred at −35° to −40° for 0.5 hours. Water (12.0 ml) was added at −35°C and the mixture stirred at this temperature for 1 hour. The slurry was warmed to 0°–5°. Water (15.0 ml) and methanol (75 ml) were added until all of the dicyclohexylamine hydrochloride dissolved. A portion of the batch (0.33 volume) was crystallized by pH adjustment with 6N ammonium hydroxide at 0°–5°. The remainder of the solution was added to the 7-ACA slurry over a 30–40 minute period maintaining the pH at 3.4–3.6. After the addition, the slurry was stirred for 1 hour at 0°–5° holding the pH at 3.6. The slurry was filtered, washed with methanol and dried at 40°–45°: 4.92 g, 79.4%. Infrared and NMR spectra were consistent for structure. The yield corrected for input cephalosporin potency is 5.15 g, 83%.

EXAMPLE 4

Preparation of 7-ACA using dicyclohexylamine

Substitution in the procedure of example 2 for the amounts of compound IIIa, $PCl_5$, $CH_2Cl_2$, dicyclohexylamine (DCHA), dichlorodimethylsilane (DDS) and methanol used therein of the amounts indicated in the following chart produced 7-ACA in the indicated yields. Each experiment was modified in some manner as to the order or mode of addition of the DCHA and/or $PCl_5$ as footnoted below the chart.

TABLE

| Compound IIIa | $PCl_5$ | DCHA | Methanol | $CH_2Cl_2$ | Actual Yield(g) | Theoretical Yield | % Yield* | Chem. Potency |
|---|---|---|---|---|---|---|---|---|
| No. 1 20.0 g | 5.22, 1.1eq. | 6.81 ml 1.5 eq. | 23.11 ml. | 170 ml. | no yield obtained | | | |
| No. 2 20.0 g | 5.22, 1.1eq. | 13.61 ml 3.0 eq. | 23.11 ml. | 170 l. | 2 gms. | 6.2 gms. | 32% | — |
| No. 3 20.0 g | 10.43, 2.2eq. | 22.68 ml 5.0 eq. | 23.11 ml. | 170 ml. | 5.52 | 6.2 | 89% | 840 mcg/mg. |
| No. 4 20.0 g | 14.23, 3.0eq. | 27.22 ml 6.0 eq. | 23.11 ml. | 170 ml. | 3.48 | 6.2 | 56.1% | 985 mcg/mg. |
| No. 5 20.0 g | 10.43g, 2.2eq. | 22.68 ml 5.0 eq. | 23.11 ml. | 170 ml. | 5.53 | 6.2 | 89% | 983/mcg/mg. |
| No. 6 20.0 g | 10.43g, 2.2eq. | 22.68 ml 5.0 eq. | 23.11 ml. | 170 ml. | 5.23 | 6.2 | 85% | 965 mcg/mg. |
| No. 7 40.0 g | 20.86g, 2.2eq. | 45.36 ml 5.0 eq. | 46.22 ml. | 400 ml. | 8.8 | 12.4 | 71% | 954 mcg/mg. |
| No. 8 20.0 g | 10.43, 2.2eq. | 22.68 ml 5.0 eq. | 23.11 ml. | 170 ml. | 5.14 | 6.2 | 83% | 962 mcg/mg. |
| No. 9 40.0 g | 20.86, 2.2eq | 45.36 ml 5.0 eq. | 46.22 ml. | 400 ml. | 10.64 | 12.4 | 86% | 966 mcg/mg. |

No. 1    $PCl_5$ added in solution as rapidly as possible, immediately followed by DCHA addition.
No. 2    $PCl_5$ added in solution as rapidly as possible, immediately followed by DCHA addition.
No. 3    $PCl_5$ in solution and base in solution added over a 20 minute period simultaneously.
No. 4    Same as No. 3.
No. 5    Base suspended in $CH_2Cl_2$ (total volume=60 mls) 16–17% or 10 mls. DCHA added, then solid, finely ground $PCl_5$, then continue dripping in base over a 20 minute period.
No. 6    Same as No.5.
No. 7    Same as No.3.
No. 8    Same as No.5.
No. 9    Same as No.5.

*Not corrected for purity of starting material or product.

EXAMPLE 5

Preparation of N-Carbisobutoxycephalosporin C di (dicyclohexylamine) salt from cephalosporin C whole broth One kg of cephalosporin C whole broth was adjusted to pH 2.0 with 30% sulfuric acid. Filter aid was added and the slurry was filtered through a precoated Buchner filter. The cake was washed with water to a filtrate and wash volume of 1500 ml.

One-fourth volume (375 ml) of acetone was added to the filtrate and washes and the mixture was adjusted to pH 8.0–8.2 with 10% NaOH while cooling to 0°–5°C.

While maintaining the pH at 8.0 with 10% NaOH on an automatic titrator, 15 ml of isobutyl chloroformate dissolved in 45 ml of acetone dried over molecular sieves was dripped in during 60-minutes time. The mixture was held at pH 8.0 for another 30 minutes at 0°–5° C. Assays showed <2% residual cephalosporin C and 94% yield of N-Carbisobutoxycephalosporin C.

1500 ml of methylisobutylketone (MIBK) was added to the acylated mixture. The pH was adjusted to 2.0 with 30% sulfuric acid and the emulsion was stirred for 10 minutes at 0°–5° C. The layers were then separated using a DeLaval centrifuge. The aqueous layer was extracted again with 500 ml of fresh MIBK for 5 minutes and separated in the centrifuge. The two rich MIBK extracts were combined and polishfiltered through filter aid. The clear filtrate was vacuum concentrated at 40° C to 400 ml. To the 400 ml of concentrate, 25 ml of water was added. The pH was adjusted to 4.5 with dicyclohexylamine and the mixture was stirred for 1–2 hours at 25°–30°C during which time a thick slurry of crystals was obtained. The pH was then adjusted to 5.0–6.0 with dicyclohexylamine and the slurry was stirred another 2 hours at 25°–30°C. The slurry was then filtered and the crystals washed thoroughly with MIBK and then with acetone. After vacuum drying at 45°C for 16 hours, the yield of dry, crystalline N-carbisobutoxycephalosporin C di (dicyclohexylamine) salt was 75% of theory based on the whole broth assay.

Variations in the above procedure have given equivalent or improved results. Successful variations have been adjustment of whole broth to pH 4 instead of 2 with sulfuric acid, adjustment of whole broth to pH 4 with oxalic acid, and crystallization of concentrate at pH 5.0 or 5.5 instead of 6.0.

EXAMPLE 6

Preparation of 7-aminocephalosporanic acid from monosodium N-carbisobutoxycephalosporin C and dicyclohexylamine (see U.S. Pat. No. 3,573,296 for starting material)

Sodium N-carbisobutoxycephalosporin C (13.5 g.), 90 ml of methylene chloride and 5.0 ml of dicyclohexylamine are mixed together. Dichlorodimethylsilane (6.2 ml) is added with stirring at about room temperature and stirring is continued for about 30 minutes. The slurry is then cooled to −60° C and 12 grams of phosphorus pentachloride dissolved in 100 ml of methylene chloride is added. An additional 11.0 of dicyclohexylamine is added while the temperature is kept below −40°C. The temperature is lowered to below −60°C and 60 ml of methanol (−70°C) is added slowly. The temperature is kept below −40°C. Subsequently, 55 ml of water is added slowly, allowing the temperature to rise. The mixture is kept cooled to about 0°C. Ammonium hydroxide is added slowly to raise the pH to about 3.6. The precipitate which forms is collected by filtration is 7-ACA.

EXAMPLE 7

Preparation of 7-ACA from N-phthaloylcephalosporin C-dibenzyl ester

N-Phthaloylcephalosporin C-dibenzyl ester (11.38 mmoles) is dissolved in 50 ml of methylene chloride and cooled to −45° C. Dicyclohexylamine (5.73 ml., 27.77 mmoles) is added followed by 3 g (14.23 mmoles) of finely ground $PCl_5$ with stirring and continued cooling below −45°C. The chlorination mix is cooled to −60°C after about 15 minutes, and 40 mls of precooled methanol (−70°C) is added all at once. Stirring is continued about 2 hours.

Ice cold 50% aqueous methanol is added (16.8 ml) and the temperature is held below −10° C for 25 minutes. The mixture is warmed to about 0°C and adjusted to pH 3.3 with ammonium hydroxide. The organic solvents are removed in vacuo and the aqueous phase is extracted with benzene and ethyl acetate (2:1). The organic phase is extracted with 3% aqueous phosphoric acid and this solution is adjusted to pH 8.5 and then extracted with ethyl acetate. The ethyl acetate phase containing the 7-aminocephalosporanic acid benzyl ester is dried over sodium sulfate, filtered and taken to dryness to yield the desired 7-aminocephalosporanic acid benzyl ester.

EXAMPLE 8

Preparation of 7-ACA and 7ADCA from various blocked cephalosporin C derivatives

Substitution in the general procedure of example 7 for the N-phthaloylcephalosporanic C dibenzyl ester used therein of equimolar quantities of 1 N-phenylacetylcephalosporin C-dibenzyl ester,
2. N-carbobenzoxycephalosporin D-dibenzyl ester,
3. N-2,4-dinitrophenylcephalosporin C-dibenzyl ester,
4. N-benzoylcephalosporin C-dibenzyl ester,
5. N-phthaloylcephalosporin C-di-(para-methoxybenzyl ester,
6. N-phthaloylcephalosporin C-dibenzhydryl ester,
7. N-phthaloylcephalosporin C-di (tetrahydropyron-2-yl ester)
8. N-2,4-dinitrophenylcephalosporin C-di (paranitrophenyl ester),
9. 7-[4-(1-phenyl-2-thiono-5-oxoimidazoolidine-4-yl)-butyryl]aminocephalosporanic acid methyl ester,
10. 7-(phenylacetamido)cephalosporanic acid benzhydryl ester,
11. 7-(phenylacetamido)-3-methyl-3-cephem-4-carboxylic acid benzhydryl ester,
12. 7-(phenylacetamido)-3-methyl-3-cephem-4-carboxylic acid methoxymethyl ester,
13. N-phthaloylcephalosporin C di (trichloroethylester), or
14. 7-(phenoxyacetamido)-3-methyl-3-cephm-4-carboxylic acid methoxymethyl ester produces respectively 1'. 7-aminocephalosporanic acid benzyl ester,
2'. 7-aminocephalosporanic acid benzyl ester,
3'. 7-aminocephalosporanic acid benzyl ester,
4'. 7-aminocephalosporanic acid benzyl ester,
5'. 7-aminocephalosporanic acid p-methoxybenzyl ester,
6'. 7-aminocephalosporanic acid benzhydryl ester,
7'. 7-aminocephalosporanic acid tetrahydropyran-2-yl ester,
8'. 7-aminocephalosporanic acid p-nitrophenyl ester,
9'. 7-aminocephalosporanic acid methyl ester,
10'. 7-aminocephalosporanic acid benzhydryl ester,
11'. 7-amino-3-methyl-3-cephem-4-carboxylic acid benzhydryl ester,
12'. 7 -amino-3-methyl-3-cephem-4-carboxylic acid methoxymethyl ester, 13'. 7-aminocephalosporanic acid trichloroethyl ester, and
14'. 7-amino-3-methyl-3-cephem-4-carboxylic acid methoxymethyl ester.

EXAMPLE 9

Preparation of 7-ACA via silyl ester and dicyclohexylamine or diisopropylamine

N-Carbisobutoxycephalosporin C (34.14 mmoles) as the free acid is added to 150 ml of methylene chloride, followed by dicyclohexylamine (75 mmoles) or diisopropylamine (75 mmoles), subsequently followed by 10.5 ml of dichlorodimethylsilane over a ten minute period with stirring. The resultant slurry is aged 30 minutes with vigorous stirring and then brought to 240 ml with additional methylene chloride.

A one-third portion of the slurry is cooled to 45°C and then treated with 27.77 mmoles of dicyclohexylamine or diisopropylamine (the same one as is used above in the silyl ester formation). The $PCL_5$, methanol and water steps are conducted in a manner identical to that used in example 1 to produce 7-ACA.

EXAMPLE 10

Preparation of 7-ACA from various blocked cephalosporin C derivatives

Substitution in the procedure of Example 9 for the N-carbisobutoxycephalosporin C used therein of an equimolaar quantity of
1. N-phenylacetylcephalosporin C,
2. N-carbobenzoxycephalosporin C,
3. N-benzoylcephalosporin C,
4. N-phthaloylcephalosporin C,
5. N-2,4-dinitrocephalosporin C,
6. N-chloroacetylcephalosporin C,
7. N-acetylcephalosporin C,
8. N-(N'-butylcarbanoyl)cephalosporin C,
9. N-(N'-p-methylphenylcarbanoyl)cephalosporin C,
10. N-(N'-isopropylcarbanoyl)cephalosporin C,
11. N-(N'-isobutylcarbanoyl)cephalosporin C,
12. N-(N'-phenylcarbanoyl)cephalosporin C,
13. N-trichloroacetylcephalosporin C produces 7-ACA.

EXAMPLE 11

Preparation of 7-ADCA 7-(Phenoxyacetamido)-3-methyl-3-cephem-4-carboxylic acid (11.38 mmoles) is dissolved in 80 ml of methylene chloride. Dicyclohexylamine or diisopropylamine (13 mmoles) is added with stirring and 1.75 ml of dichlorodimethylsilane is added. After stirring for 30 minutes, the mixture is cooled to −45° C and an additional 27.77 mmoles of the same amine as used above is added followed by 3 g of finely powdered $PCl_5$.

The remaining steps of the reaction and workup are identical to those in example 1 to produce 7-amino-3-methyl-3-cephem-4-carboxylic acid.

EXAMPLE 12

Preparation of 7-ADCA

Substitution in the procedure of example 11 for the 7-(phenoxyacetamido)-3-methyl-3-cephem-4-carboxylic acid used therein of an equimolar quantity of 7-(phenylacetamido)-3-methyl-3-cephem-4-carboxylic acid produces 7-ADCA.

We claim:
1. In the process for the preparation of a compound having the formula

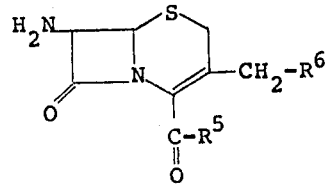

in which $R^6$ is H or acetoxy and $R^5$ is OH or the residue of an acid blocking group, which process comprises treating a compound having the formula

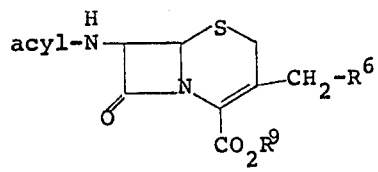

XX in which $R^6$ is H or acetoxy, $CO_2R^9$ is a carboxyl group blocked to convert it into a group not reacting with the acid halide used for forming the imino-halide, and acyl is the residue of a carboxylic acid; with an acid halide to form an imino-halide, converting the imino-halide into an imino-ether by means of treating the imino-halide with an alcohol and splitting the imino-ether double bond with a compound containing a hydroxy group; the improvement of which comprises using diisopropylamine or dicyclohexylamine as the acid scavenger in the imino-halide forming step.

2. A process of claim 1 for the preparation of a compound having the formula

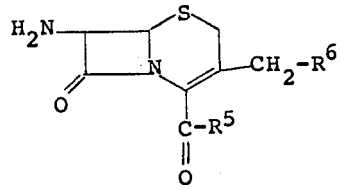

in which $R^6$ is H or acetoxy, and $R^5$ is —OH or —OY in which Y is alkyl of 1 to 10 carbon atoms, a radical of the formula

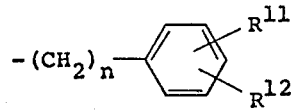

in which $n$ is an integer of 0 to 6 and $R^{11}$ and $R^{12}$ are alike or different and each is H, Cl, Br, F, $NO_2$, (lower)aklyl or (lower)alkoxy, or Y is 2,2,2-trichloromethyl, methoxymethyl or pivaloyloxymethyl; which process comprises treating a compound having the formula

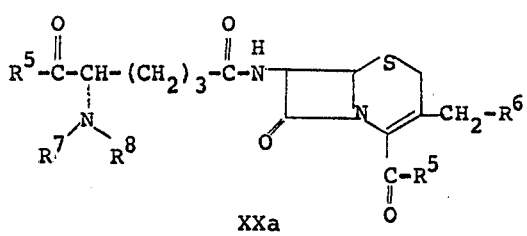

XXa or

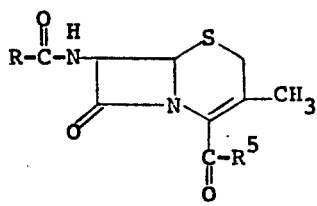

wherein $R^6$ is H or acetoxy, R is the side chain of a known fermentable penicillin, $R^7$ is H, $R^8$ is alkanoyl of 2 to 20 carbons, but preferable 2 to 6 carbons, or $R^8$ is a radical of the formula

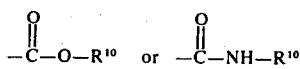

in which $R^{10}$ is alkyl of 1 to 6 carbons or a group of the formula

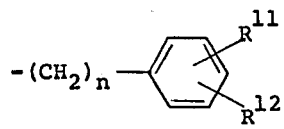

wherein n is an integer of 0 to 6 and $R^{11}$ and $R^{12}$ are alike or different and each is H, Cl, Br, F, $NO_2$, (lower)alkyl or (lower)alkoxy, or $R^8$ is trichloroacetyl, chloroacetyl, phenylacetyl or benzoyl, or when $R^7$ and $R^8$ are taken together an o-phthaloyl group; $R^5$ is —OY in which Y is alkyl of 1 to 10 carbon atoms, a radical of the formula

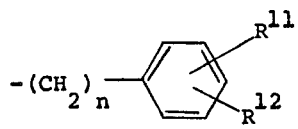

in which n is an integer of 0 to 6 and $R^{11}$ and $R^{12}$ are alike or different and each is H, Cl, Br, F, $NO_2$, (lower)alkyl or (lower)alkoxy; or Y is —$CH_2$—$CCl_3$, methoxymethyl, pivaloyloxymethyl,

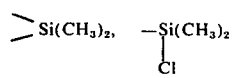

or -Si($CH_3$)$_3$; with an acid halide to form an imino-halide, converting the imino-halide into an imino-ether by means of treating the imino-halide with an alcohol, and splitting the imino-ether double bond by the addition of water; the improvement of which comprises using diisopropylamine or dicyclohexylamine as the acid scavenger in the imino-halide forming step.

3. A process of claim 1 for the preparation of a compound having the formula

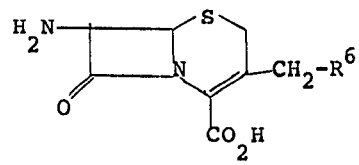

in which $R^6$ is H or acetoxy; which process comprises treating a compound having the formula

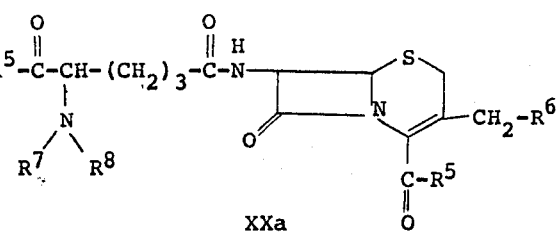

XXa and

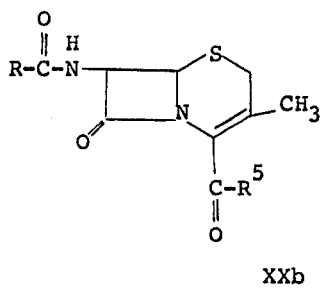

XXb wherein $R^6$ is H or acetoxy, R is phenoxymethyl or benzyl, $R^7$ is H, $R^8$ is alkanoyl of 2 to 6 carbons, a radical of the formula

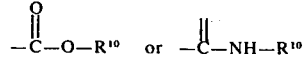

in which $R^{10}$ is alkyl of 1 to 6 carbons or a group of the formula

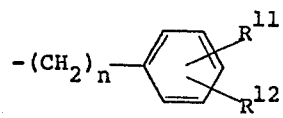

wherein n is an integer of 0 to 6 and $R^{11}$ and $R^{12}$ are alike or different and each is H, Cl, Br, F, $NO_2$, (lower)alkyl or (lower)alkoxy; or $R^8$ is trichloroacetyl, chloroacetyl, phenylacetyl or benzoyl, or when $R^7$ and $R^8$ are taken together an o-phthaloyl groupl and $R^5$ is

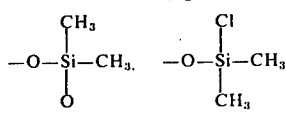

or

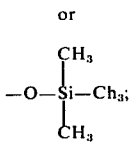

with an acid halide to form an iminohalide, converting the imino-halide into an imino-ether by means of treating the imino-ether with a (lower)alkanol, and splitting the imino-ether double bond by treatment with water; the improvement of which comprises using diisopropylamine or dicyclohexylamine as the acid scavenger in the imino-halide forming step.

4. The process of claim 3 for the preparation of 7-aminocephalosporanic acid from compound XXa in which $R^6$ is acetoxy, $R^7$ is H, $R^8$ is carbisobutoxy, $R^5$ is

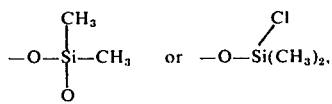

the solvent of reaction is methylene chloride, the acid halide is phosphorus pentachloride, the (lower)alkanol is methanol and the acid scavenger is dicyclohexylamine.

5. The process of claim 3 for the preparation of 7-amino-3-methyl-3-cephem-4-carboxylic acid from compound XXb in which R is phenoxymethyl, $R^5$ is

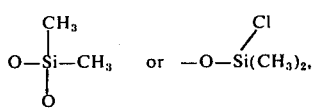

the solvent of reaction is methylene chloride, the acid halide is phosphorus pentachloride, the (lower)alkanol is methanol and the acid scavenger is dicyclohexylamine.

6. The process of claim 1 wherein the temperature is maintained below −20°C. during the formation of the imino-halide and its subsequent conversion to the imino-ether.

7. The process of claim 1 wherein the temperature is maintained below −40°C. during the formation of the imino-halide and its subsequent conversion to the imino-ether.

8. The process of claim 4 wherein the temperature is maintained below −20°C. during the formation of the imino-halide and its subsequent conversion to the imino-ether.

9. The process of claim 4 wherein the temperature is maintained below −40°C. during the formation of the imino-halide and its subsequent conversion to the imino-ether.

10. The process of claim 5 wherein the temperature is maintained below −20°C. during the formation of the imino-halide and its subsequent conversion to the imino-ether.

11. The process of claim 5 wherein the temperature is maintained below −40°C. during the formation of the imino-halide and its subsequent conversion to the imino-ether.

* * * * *

UNITED STATES PATENT OFFICE
CERTIFICATE OF CORRECTION

Patent No. 3,932,392                    Dated January 13, 1976

Inventor(s) David A. Johnson et al            Page 1 of 3

It is certified that error appears in the above-identified patent and that said Letters Patent are hereby corrected as shown below:

In the claims, please change the following claims to read as follows:

3. A process of claim 1 for the preparation of a compound having the formula

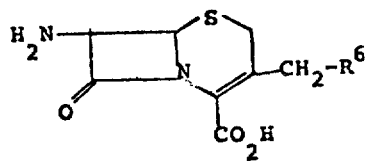

in which $R^6$ is H or acetoxy; which process comprises treating a compound having the formula

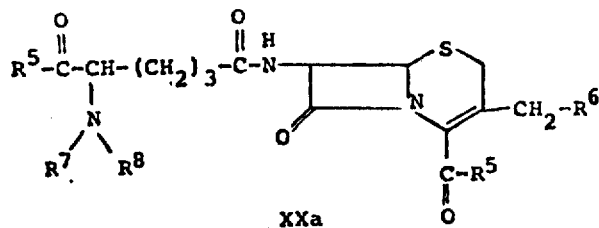

XXa and

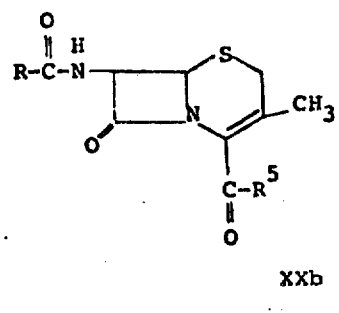

XXb wherein $R^6$ is H or acetoxy, R is phenoxymethyl or benzyl, $R^7$ is H, $R^8$ is alkanoyl of 2 to 6 carbons, a radical of the formula

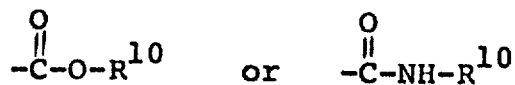

in which $R^{10}$ is alkyl of 1 to 6 carbons or a group of the formula

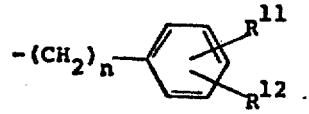

wherein n is an integer of 0 to 6 and $R^{11}$ and $R^{12}$ are alike or different and each is H, Cl, Br, F, $NO_2$, (lower)alkyl or (lower)alkoxy; or $R^8$ is trichloroacetyl, chloroacetyl, phenylacetyl or benzoyl, or when $R^7$ and $R^8$ are taken together an o-phthaloyl group; and $R^5$ is

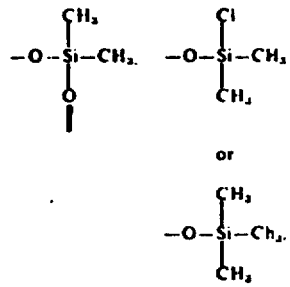

with an acid halide to form an iminohalide, converting the imino-halide into an imino-ether by means of treating the imino-ether with a (lower)alkanol, and splitting the imino-ether double bond by treatment with water; the improvement of which comprises using diisopropylamine or dicyclohexylamine as the acid scavenger in the imino-halide forming step.

5. The process of claim 3 for the preparation of 7-amino-3-methyl-3-cephem-4-carboxylic acid from compound XXb in which R is phenoxymethyl, $R^5$ is

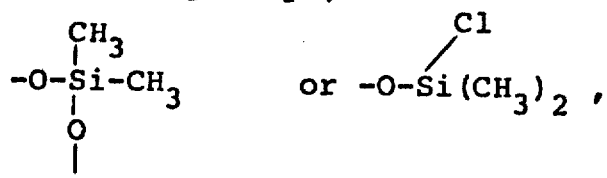

the solvent of reaction is methylene chloride, the acid halide is phosphorus pentachloride, the (lower)alkanol is methanol and the acid scavenger is dicyclohexylamine.

Signed and Sealed this sixth Day of April 1976

[SEAL]

Attest:

RUTH C. MASON
*Attesting Officer*

C. MARSHALL DANN
*Commissioner of Patents and Trademarks*